United States Patent [19]

Wolff et al.

[11] Patent Number: 4,747,838
[45] Date of Patent: May 31, 1988

[54] SYRINGE

[76] Inventors: Heinz S. Wolff, 53 Meadway, London NW11; David W. Hawes, 40 Leighfield, Mortimer, Reading, Berks, both of England

[21] Appl. No.: 7,730
[22] Filed: Jan. 28, 1987
[30] Foreign Application Priority Data Feb. 4, 1986 [GB] United Kingdom ............... 8602733

[51] Int. Cl.$^4$ .............................................. A61M 5/315
[52] U.S. Cl. ...................................... 604/218; 604/135
[58] Field of Search ............... 604/218, 187, 132, 133, 604/134, 135, 229, 236, 131

[56] References Cited

U.S. PATENT DOCUMENTS 4,209,014 6/1980 Sefton ................................ 604/132
4,507,115 3/1985 Kambara et al. .................. 604/135

Primary Examiner—John D. Yasko
Attorney, Agent, or Firm—Cohen, Pontani & Lieberman

[57] ABSTRACT

A syringe capable of remote and/or automatic control. The syringe comprises a housing defining a main chamber, a piston at one end of the chamber and biasing means for urging the piston toward the other end of the chamber, and an opening into the chamber for liquid to pass. The piston is prevented from moving by a fusible element seated on the piston and on a fuse stop for preventing the movement. A heater is provided near the fuse stop which, when energized, melts that end of the fusible element to reduce its length and thereby permit movement of the piston under the urging of the biasing means. In this way injection or aspiration is accomplished.

The heater may be energized and deenergized at will and when deenergized the fusible element ceases to be melted and the movement of the piston stops. This results in a syringe which can be turned on and off, which can inject or aspirate different and selected amounts of liquid depending upon the amount of time the heater has been on, and which can be operated for either injection or aspiration a plurality of times during the stroke from end of the chamber to the other.

In a preferred embodiment, the heater and fuse stop are one and the same element.

20 Claims, 1 Drawing Sheet

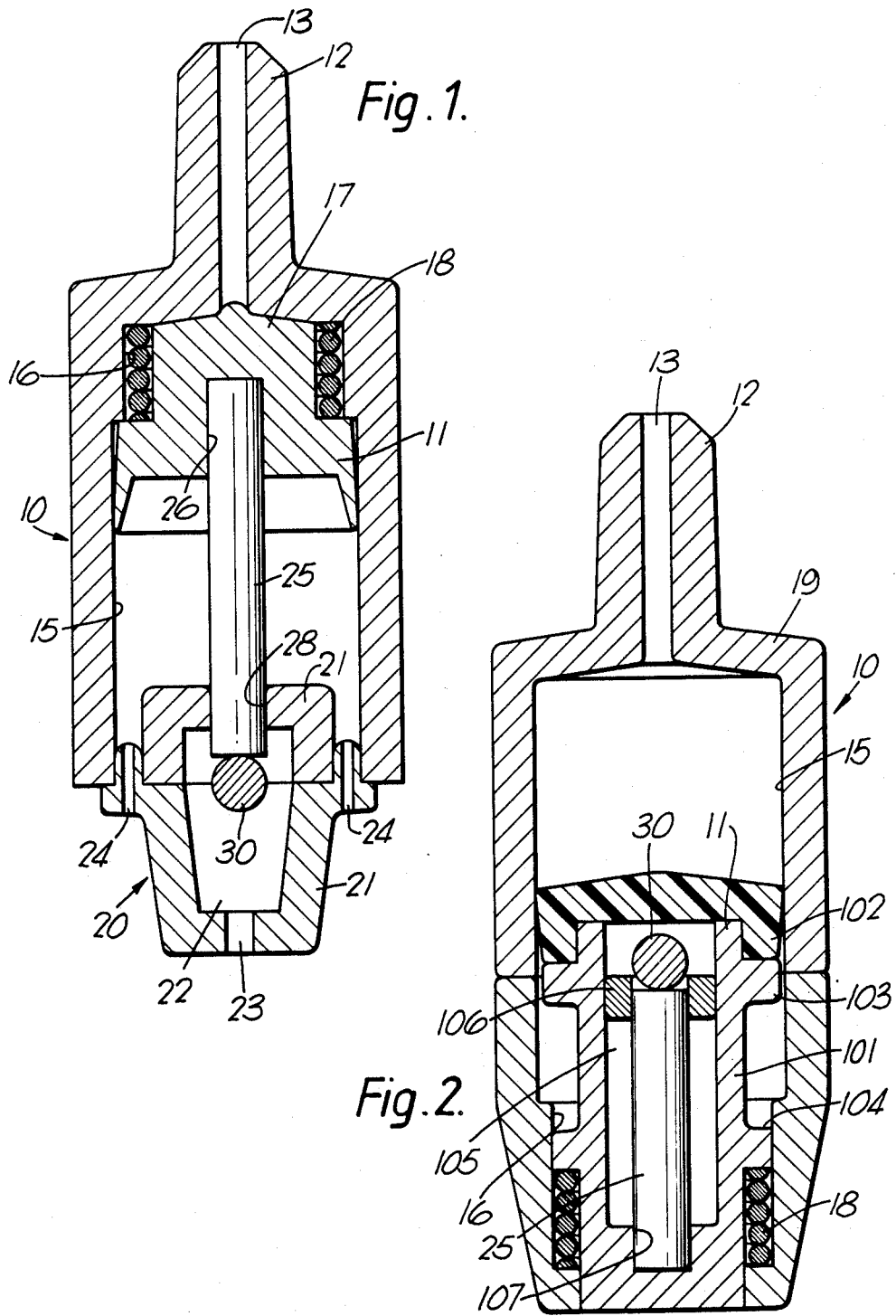

SYRINGE

BRIEF SUMMARY OF THE INVENTION

This invention relates to syringes, and especially to syringes for the collection of samples of body fluids from, or for the injection of medication into, a patent, and especially to a syringe which is capable of automatic or remote-controlled operation which may be for a full syringe stroke, or a part or a full stroke, and which may be started and interrupted pursuant to a program.

This invention in one preferred form, comprises a sampling syringe including a chamber having an opening and a piston at one end which is urged towards the other end by a spring or other biasing means, a rod-like fusible element of lowmelting point material holding the piston at said one end of the chamber against said urging or bias and at the other end of the chamber a heater to progressively melt the fusible element, the fusible element extending between the piston and the heater so as to allow movement of the piston to the extent that the heater melts said element, movement of the piston drawing liquid into, or expelling it from, the chamber through said opening. The parts may be rearranged to provide an injecting syringe.

Preferably, and as described below, the syringe is small enough to be worn by a patient without discomfort, capable of automatically collecting and storing a sufficient sample from the patient, and easily removable.

The syringe as a whole may be disposable. Alternatively, the chamber housing may be disposable but the remainder of the syringe including an end cap and the heating element disposed therein may be re-used after melting out the melted fuse material, as by, for example, immersing it in hot water.

BRIEF DESCRIPTION OF THE DRAWING

In the drawing:

FIG. 1 is a diagrammatic longitudinal section of a sampling or aspirating syringe embodying one form of the present invention; and FIG. 2 is a view similar to FIG. 1 showing a syringe for injecting medication or the like into a patient.

DETAILED DESCRIPTION OF THE PREFERRED EMBODIMENT

In the following description, references to "upper" and "lower" are for convenience of description. The syringes of this invention can be and in fact are used in any orientation.

Referring now to FIG. 1 in detail, the syringe there shown is for extracting material such as, for example, a blood sample from a patient and comprises a hollow housing 10 defining a main chamber 15 which contains a piston 11. Said hollow housing has at its upper end an axial integral extension 12 here shown as cylindrical in cross-section, as is preferred but not required, with a passage therethrough to provide an inlet 13 into a chamber 15. Preferably (although not necessarily) and as shown, the chamber 15 has a main bore and a counterbore 16. The piston 11 forms a seal with the main bore 15 and has an extension 17 to extend within the counterbore. To aid in effecting the seal, piston 11, or at least that portion engaging the wall of housing 10, may be made of elastomeric material if desired. A compression spring 18 abuts the upper end 19 of the housing 10 and seats on the piston 11 about the extension 17, to urge the piston downwardly.

At the bottom end of the chamber 15 is secured an end cap 20 having an upper wall 21 and defining a second chamber 22. For reasons which will become apparent hereafter, end cap 20 is preferably removably mounted on chamber 10 as by threads (not shown). The end cap 20 has a central vent 23 in its bottom to vent chamber 22, and vents 24 for venting chamber 15.

A fusible element 25, here shown in the form of a rod, is seated in an axial hole 26 in the piston 17 and extends into the end chamber 22 through a hole 28 in the wall 21, which serves as a guide. A heater 30 is fixedly mounted in the end chamber 22, is preferably in abutting relation with the lower end of the fusible element 25. Indeed, preferably although not necessarily, it is heater 30 which prevents the fusible element from moving downward into chamber 22 under the urging of spring 18 in the illustrated embodiment. Alternatively, a separate stationary fuse stop may serve to engage the lower end of fusible element 25 in which case the heater will be located in close heating relation with the end of the fusible element 25 resting on said fuse stop for heating and ultimately melting said end, as will be later described. As shown and presently preferred, the fuse stop and heater are one and the same.

When the heater 30 is energized and warms up to a predetermined temperature, it melts that portion of the fusible element that rests upon it, at a rate determined in part at least by the applied wattage. The piston 11 under the influence of the spring 18 moves downwardly to force unmelted fusible material 25 into abutment with the heater 30 while already melted fusible material collects in the chamber 22. Piston movement can be stopped at any point by deenergizing heater 30 and then later restarted as desired by subsequent reenergization. It is the piston movement which aspirates a sample into the chamber 15 above the piston. Therefore, clearly, the action of the syringe can be automatically, remotely and finely controlled since there are two parameters available for controlling any preset structure, wattage supplied to the heater and the time duration of such energy supply. If it is desired to aspirate rapidly a high wattage may be supplied to the heater which will heat up rapidly and rapidly melt the fusible rod 25, whereby to result in rapid downward movement of piston 11 for rapid aspiration of the sample. This aspiration can continue for as long as the supply to the heater is continued or until chamber 15 is filled with the sample. However, if the energy supplied to the heater is interrupted, the heater will cool, the melting of fusible rod 25 will stop and aspiration will stop. Therefore, the syringe does not require complete operation which will fill chamber 15 with an aspirated sample. The amount of fluid aspirated into the chamber 15 is controllable since the piston movement may be stopped at any time merely by deenergizing the heater 30. This results not only in a variable volume aspirator (or injector) but gives the opportunity to utilize the syringe in an intermittently operating mode for aspirating fluid and then discontinuing aspiration by deenergizing the heater and then reheating heater 30 to restart aspiration a second (or even a third or fourth) time. Similarly, when using this invention as a injector rather than an aspirator, injection can be similarly controlled. That is the volume injected can be controlled, and injection activity can be started and stopped at will (e.g. per program)

The spring force of spring 18 can be any desired amount. However, for blood extraction, 2 lbs. (approximately 1 kg) has proved satisfactory. The fusible element can be a tinlead indium eutectic: other various low melting alloys are available on the market and may be employed. Low melting plastics composition may also be used for the fusible element.

A eutectic composition, such as the tin-lead-indium eutectic, has the advantage of a well defined melting point and no plastic range. This makes possible reliable starting and stopping at intermediate points of piston travel. If the rod 25 of fusible material is secured at its upper end to the piston as shown, instead of being merely pressed against it, this yields yet a further advantage. Once the piston is stopped either at an intermediate or its final position, the metal freezes around and behind the heater, and effectively locks the piston in place. This is important when one or more full, i.e. operated syringes, remain connected to a manifold and are subjected to some negative pressure every time another syringe is fired. Locking the piston prevents any blood being withdrawn from then rather than from the manifold. This is especially pertinent in the use of this invention in the Method And Apparatus For Taking Samples From Or Administering Medication To A Patient described and claimed in Ser. No. 7678 filed Jan. 28, 1987.

The sample is safely stored in the chamber 15, until wanted. It may be refrigerated if necessary or, if desired, a preservative may be placed in the chamber before starting.

After use of the syringe, the preferably movable end cap 20 can be removed, and the fusible material melted out by immersing it in a warm environment. With an appropriate fusible element 25, hot water is suitable for melting out the fusible material. A new element can then be inserted and the syringe reset for another sample.

Low melting material is expensive and the compression force on the element 25 relatively high. The element is therefore preferably shaped to stand compression to best advantage with least material. To avoid creep in the element, the syringe can be stored with the spring unstressed, and cocked immediately before use.

The construction described with regard to FIG. 1 can be redesigned to inject a liquid, in one or more doses. Such an embodiment is illustrated in FIG. 2, where parts similar to those of FIG. 1 carry the same reference numbers.

Referring now to FIG. 2, the piston 11 is urged upwardly by compression spring 18 so that when so moved, the piston 11 will expel the contents of the chamber 15 through the extension or nozzle 12. The piston 11 comprises a stem 101 and a head 102, preferably of elastomeric material thereby making fluid-tight contact with the wall of housing 10. The stem 101 has a lateral extension 103, preferably in the form of a unitary or segmented flange, which supports the head 102. As shown, compression spring 18 acts between the bottom of the chamber and the underside of a second flange 104 on stem 101. Stem 101 is preferably hollow and of larger diameter than fusible element 25 to form a annular space 105 to accommodate the heater 30 and melted fuse. Heater 30 extends across the chamber 10 and a guide ring 106 which is mounted axially within the chamber closely below the heater. The fusible rod 25 is supported in an axial hole 107 at the bottom end of the piston stem, and extends through the guide ring 106 to rest against fuse stop, which preferably although not necessarily is the heater 30.

In operation, energizing the heater 30 melts the upper end of rod 25 and allows the spring to push the piston up, thereby discharging the contents of the chamber through the nozzle 12. As true of the FIG. 1 embodiment, the rate of discharge depends on the rate of heating. Discharge can be stopped and re-started as desired by control of the heater.

The syringe illustrated needs no motor, but can be completely controlled from a remote point, if desired automatically.

The expression "piston" as used herein includes, where the context admits, also a diaphragm and a bellows. Moreover, while springs 18 are shown and described as compression springs, it will be apparent that with minor modifications to the embodiments of FIGS. 1 and 2 which are well within the ability of the person of ordinary skill, they could be tension springs.

While there has been described and illustrated a preferred embodiment of the present invention, it is apparent that numerous alterations, omissions and additions may be made without departing from the spirit and scope of the invention thereof.

What is claimed is:

1. A syringe comprising a housing defining chamber having an opening, a piston movably mounted within and at one end of the chamber, means for biasing said piston towards the other end of said chamber, a fuse stop fixedly mounted relative to said housing, a heater disposed proximate said fuse stop, a fusible element of low-melting point material extending between said piston and said fuse stop for holding said piston at said one end of the chamber against the urging of the biasing means, said heater being located relative to said fusible element for melting the end thereof adjacent said fuse stop to allow movement of the piston under the urging of said biasing means to the extent of melting of said last mentioned end of said fusible element, movement of said piston transferring liquid between the chamber and the exterior of said syringe through said chamber opening.

2. A syringe as claimed in claim 1, wherein said fuse stop and said heater are the same element.

3. A syringe as claimed in claim 1, further comprising a guide for said fusible element, said fusible element extending into said guide and being seated on said fuse stop.

4. A syringe as claimed in claim 2, wherein a second chamber is provided at the other end of the first mentioned chamber for containing said heater, said two chambers being separated by an apertured wall defining a guide through which the fusible element extends into said second chamber to the heater, said second chamber providing a space in which melted fusible material collects clea of the heater.

5. A syringe as claimed in claim 4, further comprising an end cap, and wherein the second chamber is partially formed by said end cap.

6. A syringe as claimed in claim 1, wherein said biasing means comprises a spring.

7. A syringe as claimed in claim 6, wherein said spring is disposed between said piston and said one end of the chamber.

8. A syringe as claimed in claim 7, wherein said spring surrounds at least a portion of said piston.

9. A syringe as claimed in claim 1, wherein said material of the fusible element is selected so that said fusible element is meltable by said heater at a predetermined rate enabling the resulting movement of said piston to be selectively stopped and restarted for selective stopping and restarting of the transfer of liquid between said chamber and the exterior of said syringe through said chamber opening.

10. A syringe as claimed in claim 1, wherein said opening communicates directly with said chamber.

11. A syringe as claimed in claim 1, wherein said opening is defined at said one end of the chamber.

12. A syringe as claimed in claim 1, wherein said opening is defined at said other end of the chamber.

13. A syringe as claimed in claim 1, wherein said piston is disposed for sliding movement within said chamber.

14. A syringe as claimed in claim 1, wherein said piston is disposed for movement between said one end and said other end of the chamber.

15. A syringe as claimed in claim 14, wherein said piston is disposed for sliding movement within and along said chamber.

16. A syringe as claimed in claim 1, wherein said fusible element has an initial predetermined length selected so that the piston is movable within said housing between a first position at said one end of the housing and a second position at which said fusible element is fully melted.

17. A syringe as claimed in claim 16, wherein in said second position of the piston the piston abuts said fuse stop.

18. A syringe as claimed in claim 1, wherein said fusible element is carried on said piston.

19. A syringe as claimed in claim 1, wherein said fusible element projects outwardly from said piston.

20. A syringe as claimed in claim 1, wherein said fusible element projects outwardly from said piston toward said other end of the chamber.

* * * * *